US006193971B1

(12) United States Patent
Hofmann et al.

(10) Patent No.: US 6,193,971 B1
(45) Date of Patent: Feb. 27, 2001

(54) DICTYOCAULUS VIVIPARUS ANTIGEN FOR DIAGNOSING LUNGWORM INFESTATION AND FOR VACCINATION

(75) Inventors: Joachim Hofmann, Bad Camberg; Karlheinrich Schmid, Hofheim, both of (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 08/786,455

(22) Filed: Jan. 21, 1997

(30) Foreign Application Priority Data

Jan. 19, 1996 (DE) .............................................. 196 01 754

(51) Int. Cl.[7] ........................... G01N 33/53; A61K 39/00

(52) U.S. Cl. .................................... 424/191.1; 424/185.1; 424/265.1; 424/266.1; 424/276.1; 435/7.1; 436/518; 530/300; 530/350

(58) Field of Search .................................... 530/350, 300, 530/403, 412, 413; 424/184.1, 185.1, 191.1, 265.1, 276.1, 266.1; 435/69.1, 7.1; 436/518

(56) References Cited

U.S. PATENT DOCUMENTS 4,879,213 * 11/1989 Fox et al. .

OTHER PUBLICATIONS

Jørgensen, R.J., "Epidemiology of Bovine Dictyocaulosis in Denmark," *Vet. Parasitol.*, vol. 7, pp. 153–167 (1980).

Jacobs, D.E. et al., "Interactions between chemoprophylaxis and immunity to bovine parasitic gastroenteritis and bronchitis: pilot studies using an oxfendazole pulse release bolus," *Res. Vet. Sci.*, vol. 43, pp. 273–275 (1987).

Tovey, E.R. et al. "Comparison of semi–dry and conventional tank–buffer electrotransfer of proteins from polyacrylamided gels to nitrocellulose membranes," *Electrophoresis*, vol. 8, pp. 384–387 (1987).

Boch, J. et al., Veterinarmedizinisch Parasitologie, 4., Aufl. P. Parey, Berlin, Germany, pp. 294–301 (1992).

Mehlhorn, H. et al., "Diagnose und Therapie der Parasitosen von Haus–, Nutz–und Heimtieren," 2., Aufl. Gustav Fischer Verlag, Stuttgart, Germany, pp. 223–227 (1993).

Grafner, G., "Zum epizootiologischen und jahreszeilichen Verlauf von Ostertagiose–Diktyolaulose–Erkrankungen bei Jungrinderherden in den Jahren 1980 bis 1984 in den nördlichen Weidegebieten der DDR," *Mh. Vet.–Med.*, vol. 42, pp. 178–181 (1987).

Schnieder, T., et al., "Neuere Erkenntinisse zur Ätiologie, Pathogenese und Bekämpfung der Dictyocaulose," *Wien Tierärztl. Mschr.*, vo;. 76, pp. 372–376 (1989).

Pfeiffer H., "Zur verzögerten Entwicklung des Rinderlungenwurmes, Dictyocaulus viviparus," *Wien Tierärztl Mschr.*, vol. 63, pp. 54–55 (1976).

Bellmer, A. et al., "Seroepidemiological Survey on the Occurrence of *Dictyocaulus viviparus* in Lower Saxony (FRG) in First Year Grazing Calves," Proc. 13th Conf. World Ass. Adv. Vet. Parasit., Berlin, Germany, S3–10 (Aug. 11, 1989).

Wilson, R. et al., "2.2 Mb of contiguous nucleotide sequence from chromosome III of *C. elegans*," *Nature*, vol. 368, pp. 32–38 (Mar. 1994).

Schneider, T., "*Dictyocaulus viviparus*: Isolation and Characterization of a Recombinant Antigen with Potential for Immunodiagnosis," *Int. J. Parasitol.*, vol. 22, No. 7, pp.933–938 (1992).

Britton, C. et al., "Extensive diversity in repeat unit sequence of the cDNA encoding the polyprotein antigen/allergen from the bovine lungworm *Dictyocaulus viviparus*," Mol. Biochem. Parasitol., vol. 72, pp. 77–88 (1995).

Kennedy M.W. et al., "DvA–1 Polyprotein of the Parasitic Nematode *Dictyocaulus viviparus*," *J. Biol. Chem.*, vol. 270, No. 33, pp. 19277–19281 (Aug. 1995).

Britton, C. et al., "Stage–specific surface antigens of the cattle lungworm *Dictyocaulus viviparus*," *Parasite Immunol.*, vol. 15, pp. 625–634 (1993).

McKeand, J.B. et al., "Protective Immunisation of Guinea Pigs against *Dictyocaulus viviparus* using Excratory/Secretory Products of Adult Parasites," *Int. J. Parasitol.*, vol. 25, No. 1, pp. 95–104 (1995).

Basch in vaccines & World Health 1994, Oxford Univ Press, N.Y., p. 245.*

Scott et al. Mol. Biochem, Parasitol. 1989, vol. 36, 119–126.*

* cited by examiner

*Primary Examiner*—Patricia A. Duffy
(74) *Attorney, Agent, or Firm*—William M. Blackstone

(57) ABSTRACT

An immunogenic protein (DV 18) isolated from lungworm *Dictyocaulus viviparus* including variants and fragments thereof, are described. DNA encoding such protein, methods of isolating and preparing such protein, antibodies against such protein, immunoassays using such protein, a vaccine containg such protein, and methods of immunizing a mammal with such vaccine are also described.

9 Claims, 2 Drawing Sheets

DV MSP PCR Fragment Sequence

| 10 | 20 | 30 | 40 | |
|---|---|---|---|---|
| GAAGATCTAT<br>M | GGCNTCNGTN<br>A S V | CCNCCTGGAG<br>P P G D | ACATCAACAC<br>I N T | 40 |
| TCAGCCAAAC<br>Q P N | TCGAAGATCG<br>S K I V | TCTTCAACGC<br>F N A | TCCATACGAC<br>P Y D | 80 |
| GACAAGCACA<br>D K H T | CCTATCACAT<br>Y H I | CAAGATCATC<br>K I I | AACGCATCTG<br>N A S G | 120 |
| GACGTCGAAT<br>R R I | TGGATGGGCT<br>G W A | ATCAAGACCA<br>I K T T | CCAACATGAA<br>N M K | 160 |
| GAGACTTGGC<br>R L G | GTCGACCCAG<br>V D P A | CCTGCGGAGT<br>C G V | TCTTGACCCC<br>L D P | 200 |
| AAGGAGGCTA<br>K E A T | CTCTCATGGC<br>L M A | TGTGTCTTGC<br>V S C | GACACCTTCG<br>D T F E | 240 |
| AGTACGGACG<br>Y G R | TGAGGACACC<br>E D T | AACAACGACC<br>N N D R | GTATCACTGT<br>I T V | 280 |
| TGAGTGGTGC<br>E W C | AACACCCCCG<br>N T P D | ATGGCGCTGC<br>G A A | TAAGCAGTTC<br>K Q F | 320 |
| AGACGCGAGT<br>R R E W | GGTTCCAAGG<br>F Q G | AGATGGTATG<br>D G M | GTCCGCAGAA<br>V R R K | 360 |
| AGAACCTNCC<br>N L P | NATCGARTAY<br>I E Y | AAYGAATTCC<br>N E F | GG | 392 |

DICTYOCAULUS VIVIPARUS ANTIGEN FOR DIAGNOSING LUNGWORM INFESTATION AND FOR VACCINATION

BACKGROUND OF THE INVENTION

The invention relates to an antigen from the adult stages of the bovine lungworm *Dictyocaulus viviparus* (also termed *D. viviparus* or Dictyocaulus in that which follows), which antigen can be used for the immunodiagnostic detection of lungworm infestation in cattle. In a vaccine, the antigen is able to elicit immune protection against *D. viviparus*.

Lungworms are of great pathogenic and economic importance, particularly in the case of small and large ruminants. Dictyocaulus is the only lungworm which achieves sexual maturity in cattle. It is found throughout the world wherever moderate temperatures of 15–20° C. prevail at least from time to time. In Europe, *D. viviparus* is dispersed endemically in the great river meadows, in high-rainfall coastal regions and also on alpine pastures (R. J. Jörgensen (1980) Vet. Parasitol. 7, 153–167; H. Pfeiffer (1976) Wien. Tierärztl. Mschr. 63, 54–55). In the Netherlands, for example, clinical dictyocaulosis has been observed in more than 77% of calf groups which are maintained on pastures (J. Boch, R. Supperer (1992) Veterinärmedizinische Parasitologie [Veterinary Parasitology], 4th edn., Parey, Berlin, pp. 294–301.)

In calves which are exposed for the first time, the disease (dictyocaulosis) is caused by ingesting third-stage larvae together with the pasture grass. Via the bloodsteam, the larvae arrive at the alveoli of the lungs, which they penetrate in order to reach the air-carrying parts of the lung. In connection with this, lesions are produced which serve as an entry port for secondary infections due to bacteria; the multiplication of bacteria and other microbial pathogens leads to localized or generalized pulmonary inflammations with all the possible sequelae such as pulmonary edema and heart failure (T. Schnieder, A. Bellmer, F.-J. Kaup (1989) Wien. Tierärztl. Mschr. 76:372–476). Breathing is also made substantially more difficult by the presence in the upper airways of adult stages, which lead to obstructions. Diminished increases in weight, or even losses of weight, associated with growth delays are visible consequences of the marked impairment of the general state of health. From time to time, the clinical symptoms worsen dramatically and rapidly lead to death.

Lungworm disease in cattle can be diagnosed from the clinical symptomatology (G. Gräfner (1987) Monatsh. Vet. med. 42:178–181) or from the larvae which are excreted in the feces (J. Boch, R. Supperer (1992)). These options are particularly suitable for diagnosing the disease in an individual animal which is heavily infected. However, for modern large-scale animal husbandry, it is necessary to make epidemiological predictions and risk assessments, which are based on a suitable diagnosis, with regard to the outbreak of a dictyocaulosis when the grazing season is at an advanced stage; i.e. many calves, which may still only be mildly infected, have to be examined in surveys using a reliable and sensitive method. Serological methods are suitable for this purpose (A. Bellmer, T. Schnieder, A. M. Tenter (1989) Proc. 13th Conf. Wrld Ass. Adv. Vet. Parasit., p. 33, Berlin, 7.-11.8.1989). Antigens which have been identified in *Dictyocaulus viviparus* and then isolated and in some cases prepared in recombinant form are used for the serodiagnosis. Pharmaceuticals which are active against adult and juvenile stages can be employed for the curative treatment of dictyocaulosis (e.g. Levamisol®, (pro) benzimidazole, Netomin® and Ivermectin®). These preparations are highly active and are consequently usually able to prevent losses which are due to acute lungworm disease (H. Mehlhorn, D. Düwel, W. Raether (1993) Diagnose und Therapie der Parasitosen von Haus-, Nutz- und Heimtieren [Diagnosis and Therapy of the parasitoses of domestic animals, farm animals and pets]. 2nd edn. Gustav Fischer Verlag, pp. 223–227). Due to their drastic efficacy, the active compounds may not, when being used for a prophylactic/metaphylactic treatment, permit interaction of the parasite with the immune system of the host and, as a consequence, the development and maintenance of a resilient (partial) immunity. The animals are then, while still being unprotected, at the mercy of an infection in the second grazing year (COBS, D. E., S. R. Pitt, J. Förster, M. T. Fox (1987) Res. Vet. Sci. 43:273–275).

Recently, therefore, there have been ever more frequent demands for calves of the first grazing season to be immunized for epidemiological reasons, either by means of a low-grade subclinical infection or by means of vaccination. At present, only one live vaccine, in the form of X-ray attenuated larvae, is available, with this vaccine evoking a basal immunity which has to be maintained by subsequent natural infection (Mehlhorn H., et al., (1993)). If subsequent immunization by means of natural infection is insufficient, breakdowns, associated with coughing and disease, occasionally occur in connection with sudden, massive exposure. Since the vaccine itself only keeps in a refrigerator for about 3 weeks, it must be stored carefully and used rapidly. This procedure prevents any "surface-covering" use; the vaccine is therefore first and foremost reserved for particular endemic regions. Because of the inadequate stability and quality, there is a need to develop defined vaccines (subunit vaccines).

SUMMARY OF THE INVENTION

The object therefore presented itself of removing the cited disadvantages of the current vaccination method by preparing a novel, advantageous vaccine.

It is a further object of the present invention to provide a novel antigenic protein invoking an immunogenic response in cattle and other mammalian species.

It is a further object of this invention to provide a means for producing such proteins recombinantly.

In accomplishing the foregoing objects, there has been provided, an immunogenic protein, DV 18, or an immunogenic fragment thereof, wherein the protein has a molecular weight of between approximately 16000 and 19000 daltons, and has an isoelectric point of between approximately 5.2 and 5.8.

There is further provided, an immunogenic DV 18 protein or a fragment thereof, comprising the amino acid sequences as shown in Table 1.

There is further provided, a DNA molecule which encodes an immunogenic protein, DV 18, or an immunogenic fragment thereof, wherein the protein comprises the amino acid sequences as shown in Table 1.

There is further provided, a recombinant protein which comprises the amino acid sequences as shown in Table 1, or immunogenic variants thereof.

BRIEF DESCRIPTION OF THE FIGURE

414 nm; X axis: Days. Antigen was administered at the beginning of the experiment and on the 21st day; *Dictyocaulus viviparus* 3 larvae were administered on the 28/29th day (challenge). The antiserum dilution for the measurement was 1:200. Details of this experiment are given in Example 11.

DETAILED DESCRIPTION OF PREFERRED EMBODIMENTS

The invention in one embodiment relates to a novel, immunogenic native protein, termed DV 18, which was isolated from adult *Dictyocaulus viviparus* worms. Its immunogenicity is based, in particular, on the fact that, after having been administered subcutaneously in cattle, it induces an antibody response which confers immune protection on the animal. In addition, this protein can be used in an ELISA or in other immunoassays known to those of skill in the art for the retrospective immunodiagnosis of dictyocaulosis in cattle. DV 18 is characterized by the following physical properties. The protein is stable in all buffers used. No decrease in immunoreactivity was observed after the purified antigen had been deep-frozen (−85° C.). Using an FPLC system and an analytical gel filtration column (Superose 12 HR 10/30), a retention volume of 13.5 ml was measured for antigen DV 18 (elution buffer: phosphate-buffered sodium chloride solution, pH 7.4). The protein possesses essentially no N-glycosidically bonded carbohydrate structures of the "high- mannose" or "hybrid" type, any O-glycosidically bonded carbohydrate chains or any complex, sialyzed carbohydrate chains and is obviously essentially not glycosylated. In an SDS polyacrylamide gel (Phastgel 8–25%), DV 18 has an estimated molecular weight of approximately 17 500 daltons. The isoelectric point of DV 18 is in the range of 5.2–5.85.

By sequencing Endo-Lys C enzymatically cleaved peptides of the antigen the following partial sequences were identified.

| TPPAGVFYQGXSATPIA | (SEQ ID NO.: 1) |

The amino acid adjacent to the N-terminus of SEQ ID NO. 1 is any one of the amino acids D, N, S, G or R.

| XLGVDPASGVLDPKEATLMA | (SEQ ID NO.: 2) |
| LDIEYNE | (SEQ ID NO.: 3) |

The amino acid adjacent to the N-terminus of SEQ ID NO.: 3 is any one of the amino acids N or S.

| FRREWFQGDGWRRK | (SEQ ID NO.: 4) |

The amino acid adjacent to the N-terminus of SEQ ID NO.: 4 is any one of the amino acids A or G. In addition, the 11th amino acid of SEQ ID NO.: 4(V) can also be methionine (M).

| VFNAPYDDK | (SEQ ID NO.: 5) |

The amino acid adjacent to the N-terminus of SEQ ID NO.: 5 is any one of the amino acids D or I.

| XPPAGVFYQGWSATPIANGSLG | (SEQ ID NO.: 6) |

The amino acid adjacent to the N-terminus of SEQ ID NO. 6 is any one of the amino acids D, S, G or A.

| TYHIK | (SEQ ID NO.: 7) |

The amino acid adjacent to the N-terminus of SEQ ID NO. 7 is any one of the amino acids D or H.

| IINASGRRIGWAIK | (SEQ ID NO.: 8) |

Inhibition of the development of *Dictyocaulus viviparus* in cattle following vaccination represents an outstanding biological property.

A preferred embodiment of the invention therefore relates to an immunogenic protein having a protective effect, which protein is isolated from adult worms of the lungworm *Dictyocaulus viviparus* and preferably exhibits a molecular weight of 16000 to 19000 or approximately 16000 to approximately ±19000 Da, an isoelectric point between 5.2 and 5.8, or approximately between 5.2 and 5.8, essentially no glycosylation and a N-terminal amino acid part sequence as shown in Table 1.

The invention preferably relates to a protein which has a molecular weight of 17 500±1 500 Da and/or an isoelectric point of 5.5. In another embodiment, the protein has a molecular weight of approximately 17500±1500 Da and/or an isoelectric point of approximately 5.5.

Furthermore, the protein of the present invention may comprise a mixture of different serological forms of naturally occurring DV 18 protein. In addition to DV 18 protein obtained from *Dictyocaulus viviparus* cells, the present invention includes recombinant DV 18, fragments, and variants of the naturally-occurring DV 18.

The category of DV 18 variants includes, for example, oligopeptides and polypeptides corresponding to immunogenic portions of the DV 18 polypeptide. Thus, a variant is intended to include a polypeptide that is homologous to and retains the salient immunological features of the natural DV 18 polypeptide. In this regard, "homology" between two sequences connotes a likeness short of identity indicative of a derivation of the first sequence from the second. For example, a polypeptide is "homologous" to DV 18 if it contains an amino acid sequence which corresponds to an epitope recognized by DV 18 specific antibodies or T-cells. Such a sequence may be only a few amino acids long and may be a linear determinant or one which arises when amino acids from separated portions of a linear sequence are spatially juxtaposed after protein folding or after being subjected to covalent bond modification. The amino acid sequences which are antigenic determinants for purposes of this invention can be ascertained, for example, by monoclonal mapping analysis techniques which are known in the art. See Regenmortel, *Immunology Today* 10: 266–72 (1989), and Berzofsky, et al., *Immunological Reviews* 98: 9–52 (1987). Assaying for this type of similarity can also be effected via a competitive-inhibition study in the case of antibodies or by T-cell proliferation.

Polypeptides which qualify as DV 18 variants according to these criteria can be produced, pursuant to the present invention, by conventional reverse genetic techniques, i.e., by designing a genetic sequence based upon an amino acid sequence or by conventional genetic splicing techniques. For example, DV 18 variants can be produced by techniques which involve site-directed mutagenesis or oligonucleotide-directed mutagenesis. See, for example, "Mutagenesis of Cloned DNA," in CURRENT PROTOCOLS IN MOLECULAR BIOLOGY 8.0.3 et seq. (Ausubel, et al. eds. 1989) ("Ausubel").

Other DV 18 variants within the present invention are molecules that correspond to a portion of DV 18, or a fragment thereof, or that comprise a portion of DV 18 but are not coincident with the natural polypeptide, both of which display the immunogenic activity of DV 18 when presented alone or, alternatively, when linked to a carrier. A DV 18 variant of this sort could represent an actual fragment of the natural molecule or could be a polypeptide synthesized de novo or recombinantly.

The peptide sequences of the proteins determined as above can be used to determine the DNA sequence encoding the protein. Methods for carrying out this determination are well known in the art. See, for example Sambrook et al., MOLECULAR CLONING: A LABORATORY MANUAL, Second Edition, (Cold Spring Harbor Laboratory Press, Cold Spring Harbor, N.Y. 1989).

Regions of the DV 18 amino acid sequence can be selected for construction of nucleotide probes. From the amino acid sequence, the mRNA sequence can be determined by knowledge of the genetic code. From the mRNA sequence, the coding of the DNA can be determined by knowledge of the base-pairing of nucleic acids. A probe made complementary to mRNA is useful in screening both "Southern" and "Northern" blots. Because of the degeneracy of the genetic code, the exact nucleic acid sequence cannot be precisely deduced. To minimize the number of different possibilities, regions of the amino acid sequence are chosen that are rich in amino acids with single codons (methionine: AUG: tryptophan: UGG) or double codons (phenylaianine: UUU, UUC: tyrosine: UAU, UAC: histidine: CAU, CAC). A mixture of nucleotides that contain all possible coding combinations can be chemically synthesized simultaneously by standard methods. Only one of the coding combinations will be perfectly complementary.

To select for the correct coding combination, the hybridization of the probe to the genome conditions can be adjusted to a point where only the perfectly complementary probe will be stably hybridized to the genomic DNA. Synthesis of nucleotides can be accomplished manually or by automated machines using the phosphodiester (Agarwal, et al., Angew, Chem. Int. Ed. 11:451 1972, phosphotriester (Hsiung, et al., Nucleic Acid Res. 6:1371 (1979) or phosphoramidite (Beaucage and Caruthers, Tetrahedron Lett. 22:1859 1981) methods. To identify the probe in use, the nucleotide can be labelled directly with atoms of $^{32}P$, $^{3}H$ or $^{14}C$ or fluorescers or indirectly with specific labelled antibodies.

Thus, in another embodiment, the invention relates to DNA encoding DV 18 and variants thereof. For instance, the invention also relates to a DNA which encodes a protein as described above taking into consideration the degeneracy of the genetic code.

The invention also relates to a process for isolating the DNA, in which process:
a) degenerate oligonucleotides are prepared which contain a DNA sequence derived from amino acid sequence of DV 18 or from the peptide sequences as described above;
b) the oligonucleotides which are prepared in accordance with a) are labeled radioactively or nonradioactively; and
c) cDNA clones which hybridize under stringent conditions with the hybridization probes prepared in accordance with b) are isolated from a cDNA library which is prepared from *Dictyocaulus viviparus.*

The invention furthermore relates to a process for isolating the DNA, in which process:
a) PCR primers are prepared which contain a DNA sequence derived from the amino acid sequence of DV 18 or fragments thereof, for example, the peptide sequences as described above, or which contain an oligo-dT sequence;
b) using the PCR primers which have been produced in this way, PCR fragments are generated from a cDNA library which has been prepared from *Dictyocaulus viviparus*;
c) which fragments are cloned and analyzed in accordance with current methods; and
d) used in place of the degenerate oligonucleotides to complete the cDNA sequence by means of hybridization methods as described above.

The last-described process can also be modified such that RNA is used as the template for the PCR reaction, with the RNA initially being subjected to reverse transcription in an additional step and the resulting first cDNA strand being used for the PCR.

In the above context, "stringent conditions" in connection with DNA hybridization denote preferably, 6xSSC, 68° C. or approximately 6xSSC, 68° C., although one of skill in the art would know how to vary stringency conditions depending abut the size of the DNA probe.

In a preferred embodiment of the present invention, the peptide sequences are used to design degenerate oligonucleotide primers for polymerase chain reactions. Each degenerate primer set will preferably contain every possible DNA sequence encoding the corresponding peptide sequences. Primer sets are prepared in both the sense and antisense orientation. Suitable oligonucleotide primers can be synthesized using commercial synthesizers, such as those supplied by Applied Biosystems (Foster City, Calif.). In a particularly preferred embodiment, the primers include additional nucleotide sequences containing restriction endonuclease cleavage sites. The presence of such sites allows for the directional cloning of PCR products into suitable cloning vectors after treatment with an appropriate restriction enzyme. See Finney, "Molecular Cloning of PCR Products" in CURRENT PROTOCOLS IN MOLECULAR BIOLOGY, Ausubel et al. Eds. (John Wiley & Sons, New York, 1987) p. 15.7.1.

The following primers can be used as PCR primers:
Primer 904 (SEQ ID NO: 9), forward (sense) primer encoding I/VVFNAP where I/V indicates that the amino acid in this position is either I or V:
GAAGATCTRTNGTCTTYAAYGCNCC
Primer 905(SEQ ID NO: 10), reverse (antisense) primer encoding EWFQGD:
CCGGAATTCRTCNCCCTGGAACCAYTC
Primers 906 and 907 (SEQ ID NO: 11 and 12 respectively), two reverse (antisense) primers encoding LPIEYN:
CCGGAATTCRTTRTAYTCGATNGGYAA (906)
CCGGAATTCRTTRTAYTCGATNGGNAA (907)

The IUPAC ambiguity code is used above to depict base pairs where the exact nucleic acid sequence cannot be precisely deduced due to the degeneracy of the genetic code. These primers will preferably have BglII or EcoRI restriction sites added to their 5'-ends to facilitate cloning of amplified fragments. As a template Dictyocaulus cDNA is preferably used. Additionally, this primers can be employed as probes for "Southern" or Northern"blots as described, supra.

Template DNA for the PCR can be prepared from an appropriate host cell using methods well known in the art. See Sambrook et al., supra. In a preferred embodiment, host cells are crushed under liquid nitrogen and mRNA is extracted using a commercially available kit (Pharmacia, Piscataway, N.J.).

The mRNA preparation can then be used as a template for cDNA synthesis using poly(dT) or random hexamer primers by standard techniques. See Sambrook et al., supra. In a particularly preferred embodiment, cDNA synthesis is carried out using a commercially available kit (Pharmacia).

The cDNA can then be used directly for PCR using the method of Saiki et al., *Science* 239: 487 (1988). The cDNA also is used to prepare a cDNA library by standard methods. See Sambrook et al., supra. In a particularly preferred embodiment, the cDNA is packaged into bacteriophage particles using a commercially available kit (Promega, Madison, Wis.). The packaged cDNA is then transfected into *E. coli* to produce a cDNA library.

In an alternative preferred embodiment, genomic DNA from a host cell can be used as the template DNA for the PCR. Genomic DNA can be prepared by standard methods, for example, using Triazol™, a commercial reagent available from Life Technologies, Inc. (Gaithersburg, Md.). In a particularly preferred embodiment, samples of host cells, prepared as above are extracted into a Tris-saline-EDTA-SDS buffer and the extract treated with RNAse A and Proteinase K to digest RNA and proteins. After phenol:chloroform extraction, the DNA is ethanol precipitated by standard methods and resuspended in TE buffer.

The PCR can then be used to prepare double stranded DNA molecules to probe the cDNA library and the genomic DNA for the gene(s) encoding the proteins. In a preferred embodiment, degenerate primers are prepared corresponding to the termini of the longest peptide sequence determined by peptide sequencing. In a particularly preferred embodiment, primers are used in a PCR with first strand cDNA as template to amplify the DNA encoding the peptide. PCR is carried out under standard conditions. See Sakai et al., supra.

PCR amplification products are analyzed by polyacrylamide gel electrophoresis using standard methods. If an amplification product of the expected size (based on the peptide sequence) is found, the product is digested with appropriate restriction enzymes, ligated into a cloning vector and cloned by standard methods. See Sambrook et al, supra. In a preferred embodiment, clones are sequenced to verify that sequences according to the expected peptide sequence are present.

Once the DNA sequence encoding the peptide is known, it can be used to prepare non-degenerate primers corresponding to that sequence, again containing restriction enzyme recognition sequences to aid in cloning of DNA products. These primers are used in combination with degenerate primers corresponding to other peptide sequences to generate PCR amplification products which can be cloned and then analyzed as above. By these means, fragments of the gene sequence of the protein can be determined. Alternative methods for carrying out this PCR analysis include use of the 5' or 3' RACE methods using commercially available kits, such as those manufactured by Life Technologies (Gaithersburg, Md.) or Clontech (Palo Alto, Calif.). Primers for this method are selected according to the manufacturer's directions.

Gene fragments prepared as above are excised from the cloning vector by restriction enzyme digestion, labeled with $^{32}$p by conventional methods and used as probes to identify the complete gene encoding the protein from within a cDNA library. In a preferred embodiment, the probe is chosen such that it is long enough to ensure hybridization specificity, while remaining short enough to allow reasonable rates of hybridization to the target gene.

Screening of the cDNA library is carried out by conventional methods. See Sambrook et al, supra. cDNA clones which hybridize to the probe are purified and their sequences determined. To facilitate sequencing, nested deletions in the clones can be created using standard protocols, or by commercially available kits such as Erase-a-base (Promega, Madison, Wis.) or The Deletion Factory (Life Technologies, Gaithersburg, Md.), following the manufacturer's instructions. The sequences obtained are analyzed for the presence of open reading frames by conventional methods and to check if the entire gene sequence has been found. In a preferred embodiment, cDNA libraries are prepared by both random hexamer and poly (dT) priming from samples, and are used to maximize the chances of finding the complete coding sequence of the desired gene.

Once the entire coding sequence of the gene for the protein has been determined, the gene can be inserted into an appropriate expression system. The gene can be expressed in any number of different recombinant DNA expression systems to generate large amounts of protein, which can then be purified and used to vaccinate animals to provide protection. Included within the present invention are proteins having native glycosylation sequences, and deglycosylated or unglycosylated proteins prepared by the methods described below.

Examples of expression systems known to the skilled practitioner in the art include bacteria such as *E. coli,* yeast such as Pichia pastoris, baculovirus, and mammalian expression systems such as in Cos or CHO cells. In a preferred embodiment, recombinant proteins are expressed in *E. coli,* Pichia pastoris, and baculovirus expression systems.

The complete gene for the protein can be expressed or, alternatively, fragments of the gene encoding antigenic determinants can be produced. In a first preferred embodiment, the gene sequence encoding the protein is analyzed to detect putative transmembrane isequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli,* as it leads to the production of insoluble aggregates which are difficult to renature into the native conformation of the protein. Deletion of transmembrane sequences typically does not significantly alter the conformation of the remaining protein structure. Moreover, transmembrane sequences, being by definition embedded within a membrane, are inaccessible as antigenic determinants to a host immune system. Antibodies to these sequences will not, therefore, provide immunity to the host and, hence, little is lost in terms of immunity by omitting such sequences from the recombinant proteins of the invention. Deletion of transmembrane-encoding sequences from the genes used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

In another embodiment, computer sequence analysis is used to determine the location of the predicted major antigenic determinant epitopes of the recombinant protein. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants. Once this analysis is made, polypeptides can be prepared which contain at least the essential features of the antigenic determinant and which can be employed in vaccines. Genes encoding these determinants can be constructed and inserted into expression vectors by standard methods, for example, using PCR cloning methodology.

As an alternative to recombinant polypeptides, synthetic peptides corresponding to the antigenic determinants can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides in vaccines typically requires conjugation of the peptide to an immunogenic carrier protein such as hepatitis B surface antigen. Methods for performing this conjugation are well known in the art.

In yet another embodiment, amino acid sequence variants of the protein are prepared. These may, for instance, be minor sequence variants of the protein which arise due to natural variation within the population of that host cell from which the protein is identified, or they may be homologues of the protein found in other host cell species (which are identified by the methods described below). They also may be sequences which do not occur naturally in the protein but which are sufficiently similar that they elicit an immune response when administered to a host. Sequence variants can be prepared by standard methods of site-directed mutagenesis such as those described above for removing the transmembrane sequence.

Amino acid sequence variants of the protein can be substitutional, insertional or deletion variants. Deletion variants lack one or more residues of the native protein which are not essential for immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain the exchange of one amino acid for another at one or more sites within the protein, and are designed to modulate one or more properties of the protein such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants contain fusion proteins such as those used to allow rapid purification of the protein and also can include hybrid proteins containing sequences from other proteins and polypeptides which are homologues of the protein. For example, an insertional variant could include portions of the amino acid sequence of the protein from one species, together with portions of the homologous protein from another species. Homologous proteins can be identified by the methods described below. Other insertional variants can include those in which additional amino acids are introduced within the coding sequence of the protein. These typically are smaller insertions than the fusion proteins described above and are introduced, for example, to disrupt a protease cleavage site.

In another embodiment, major antigenic determinants of the protein are identified by an empirical approach in which portions of the gene encoding the protein are expressed in a recombinant host, and the resulting proteins tested for their ability to protect host animals from challenge. For example, PCR can be used as described above to prepare a range of proteins lacking successively longer fragments of the C-terminus of the protein. The immuno activity of each of these proteins then identifies those fragments or domains of the protein which are essential for this activity. Further experiments in which only a small number of amino acids are removed at each iteration then allows the location of the antigenic determinants of the protein.

Another embodiment for the preparation of the proteins of the invention is the use of peptide mimetics. Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic protein of the present invention would, when administered to a host, elicit an immune response which would lead to recognition of the native host cell protein.

Successful applications of the peptide mimetic concept have thus far focussed on mimetics of β-turns within proteins, which are known to be highly antigenic. Likely β-turn structure within an protein of the invention can be predicted by computer-based algorithms as discussed above. Once the component amino acids of the turn are determined, mimetics can be constructed to achieve a similar spatial orientation of the essential elements of the amino acid side chains, as discussed in Johnson et al., supra. The mimetic can then be conjugated to a carrier protein for use as a vaccine, as discussed above for the synthetic peptides.

The gene or gene fragment encoding the desired polypeptide can be inserted into an expression vector by standard subcloning techniques. In a preferred embodiment, an E. coli expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.). Some of these systems produce recombinant protein bearing only a small number of additional amino acids, which are unlikely to affect the antigenic ability of the recombinant protein. For example, both the FLAG system and the 6xHis system add only short sequences, both of which are known to be poorly antigenic and which do not adversely affect folding of the protein to its native conformation. Other fusion systems produce proteins where it is desirable to excise the fusion partner from the desired protein. In a preferred embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In another embodiment, the expression system used is one driven by the baculovirus polyhedrin promoter. The gene encoding the protein can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying the gene for the protein is transfected into Spodoptera frugiperda (Sf9) cells by standard protocols, and the cells are cultured and processed to produce the recombinant protein. See Summers et al., A MANUAL OF METHODS FOR BACULOVIRUS VECTORS AND INSECT CELL CULTURE PROCEDURES, Texas Agricultural Experimental Station.

The protein expressed in any of a number of different recombinant DNA expression systems can be obtained in large amounts and tested for biological activity. By means of example only, the protein can be purified from the bacterial systems described above as follows.

The recombinant bacterial cells, for example *E. coli,* are grown in any of a number of suitable media, for example LB, and the expression of the recombinant protein induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol). At this stage it may be advantageous to incubate the protein for several hours under conditions suitable for the protein to undergo a refolding process into a conformation which more closely resembles that of the native protein. Such conditions generally include low protein concentrations less than 500 $\mu$g/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the protein can then be purified further and separated from the refolding mixture by chromatography on any of several supports including ion exchange resins, gel permeation resins or on a variety of affinity columns.

Applications of the invention include all of the uses for bases, nucleosides, nucleotides, oligonucleotides and polynucleotides, particularly those containing labels. For instance, the present invention is a useful tool in recombinant DNA and other protocols involving nucleic acid hybridization techniques.

More specifically, oligonucleotides and nucleic acids encoding a compound of the invention can be used as hybridization probes, capable of recognizing and specifically binding to complementary nucleic acid sequences, providing thereby a means of detecting, identifying, locating and measuring complementary nucleic acid sequences in a biological sample.

Biological samples include, among a great many others, blood or blood serum, lymph, ascites fluid, urine, microorganism or tissue culture medium, cell extracts, or the like, derived from a biological source, or a solution containing chemically synthesized protein, or an extract or solution prepared from such fluid from a biological source. It is further intended to include cells, tissue and other organic matter such as feces, food and plants. Examples of tissues include lung, blood, and lymph tissue.

Molecular probes containing the invention also can be used to identify nucleotide sequences to which proteins bind specifically. For instance, probes immobilized on solid supports can isolate and purify proteins which bind to sequences within the probes. Probes labeled with biotin, for example, can be bound to affinity chromatography supports, or magnetic beads bearing covalently coupled streptavidin. Proteins which bind to such biotin-labeled probes can be separated from a biological sample containing a variety of other proteins. Other methods for purifying proteins using a solid support are well known to the skilled artisan.

An oligonucleotide containing a modified nucleotide of the invention can be used as a primer to initiate nucleic acid synthesis at locations in a DNA or RNA molecule comprising the sequence complementary to the oligonucleotide sequence. The synthesized nucleic acid strand would have incorporated, at its 5' terminus, the oligonucleotide primer bearing the invention and would, therefore, be detectable by exploitation of the characteristics of the detectable label. Two such primers, specific for different nucleotide sequences on complementary strands of dsDNA, can be used in the polymerase chain reaction (PCR) to synthesize and amplify the amount of a nucleotide sequence. The detectable label present on the primers will facilitate the identification of desired PCR products. PCR, combined with techniques for preparing complementary DNA (cDNA) can be used to amplify various RNAS, with oligonucleotide primers again serving both to provide points for initiation of synthesis in the cDNA duplex flanking the desired sequence and to identify the desired product. Primers labeled with the invention may also be utilized for enzymatic nucleic acid sequencing by the dideoxy chain-termination technique.

The invention can be applied to measure or quantitate the amount of DNA or mRNA present in a sample. For instance, the concentration of nucleic acid can be measured by comparing detectable labels incorporated into the unknown nucleic acid with the concentration of detectable labels incorporated into known amounts of nucleic acid.

Such a comparative assessment can be done using biotin where the respective concentrations are determined by an enzyme-linked assay utilizing the streptavidin-alkaline phosphatase conjugate and a substrate yielding a soluble chromogenic or chemiluminescent signal.

Additionally, the instant invention relates to polynucleotide sequences which hybridize under stringent conditions to a DNA sequence encoding for natural DV 18 protein having a molecular weight of 16000 to 19000 or approximately 16000 to approximately 19000 Da, an isoelectric point between 5.2 and 5.8, or approximately between 5.2 and 5.8, and having essentially no glycosylation and having a N-terminal amino acid part sequence as shown in Table 1. Stringent conditions for such hybridization are known to those of skill in the art, see, e.g., Maniatis et al., *Molecular Cloning* (Cold Spring Harbor Press, 2d ed., 1989) chapters relating to stringent probe hybridization.

The invention furthermore relates to a process for isolating and purifying the DV 18 protein, in which process the isolation and purification is carried out, for example, using extraction methods and chromatographic methods which are known to the skilled person.

In a particular embodiment, isolation and purification of the DV 18 protein is carried out by disrupting *D. viviparus* cells and extracting supernatant from the disrupted cells, via, for example, centrifugation, to remove course tissue constituents. Then the supernatant is purified via a gel filtration column, so that a fraction of DV 18 is obtained exhibiting a molecular weight of 16000 to 19000 or approximately 16000 to approximately 19000 Da, an isoelectric point between 5.2 and 5.8, or approximately between 5.2 and 5.8, and having essentially no glycosylation and having a N-terminal amino acid part sequence as shown in Table 1. Of course other extraction and purification procedures will be readily apparent to one of skill in the art.

The invention furthermore relates to a recombinant protein containing amino acid sequences as shown in Table 1, which protein is preferably obtainable by expressing a cDNA, which has been obtained as described above, in prokaryotes or eukaryotes and then purifying the protein using methods known to the skilled person.

The invention likewise relates to an immunoassay using the above-described protein from *D. viviparus*, in which process the quantity of DV 18-specific antibodies in the blood of cattle or other mammalian hosts is determined by, for example, incubating DV 18-coated ELISA plates with bovine serum or other mammalian serum to be examined and detecting any DV 18-antibody complexes which are formed using, for example, peroxidase-conjugated, polyclonal antibodies and an appropriate color reaction which is known to the skilled person.

Other immunoassays contemplated by the present invention include direct and indirect assays, sandwich assays, solid phase assays such as those using plates or beads among others, and liquid phase assays, inter alia. Assays suitable for use in the invention include those that use primary and secondary antibodies, and those that use antibody binding reagents such as protein A. Moreover, a variety of detection methods can be used in the invention, including calorimetric, fluorescent, phosphorescent, chemiluminescent, luminescent and radioactive methods.

The invention also relates to a vaccine. In a particularly preferred embodiment, the vaccine comprises the above-described *D. viviparus* protein or fragment thereof, in conjunction with a carrier or adjuvant and, where appropriate, auxiliary substances, for immunizing cattle against dictyocaulosis.

More generally, however, the vaccine of the present invention is intended for the immunization of a susceptible mammal.

Following purification to an acceptable degree (which is generally in excess of 50% of the total peptide or protein), the antigen can then be administered to animals in the form of a vaccine. In preferred embodiments of the invention, the animals to be immunized are cattle. Where appropriate, whole cells may be used in vaccines. For example Sf9 cells or CHO cells expressing the recombinant antigen could be used directly, in live or killed form, to administer the antigen to host animals. Alternatively live viruses containing nucleic acid sequences encoding the antigens of the invention can be used in vaccines. See for example U.S. Pat. Nos. 4,769,330 and 4,603,112, the respective contents of which are hereby incorporated by reference.

The vaccine may include any of a number of different substances referred to as adjuvants, which are known to stimulate the appropriate portion of the immune system of the vaccinated animal. Suitable adjuvants for the vaccination of animals include, but are not limited to oil emulsions such as Freund's complete or incomplete adjuvant (not suitable for livestock use), Marcol 52:Montanide 888 (Marcol is a Trademark of Esso, Montanide is a Trademark of SEPPIC, Paris), squalane or squalene, Adjuvant 65 (containing peanut oil, mannide monooleate and aluminium monostearate), mineral gels such as aluminium hydroxide, aluminium phosphate, calcium phosphate and alum, surfactants such as hexadecylamine, octadecylamine, lysolecithin, dimethyldioctadecylammonium bromide, N, N-dioctadecyl—N,N'-bis (2-hydroxyethyl) -propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate.

The antigens, expression products and/or synthetic polypeptides of the present invention also can be administered following incorporation into liposomes or other microcarriers, or after conjugation to polysaccharides, proteins or polymers or in combination with Quil-A to form "Isocoms" (Immunostimulating complexes). Other adjuvants suitable for use in the present invention include conjugates comprising the immunogen together with an integral membrane protein of prokaryotic origin, such as TraT (see PCT/AU87/00107).

Routes of administration, dosages to be administered, and frequency of injections are all factors which can be optimized using ordinary skill in the art. Typically, the initial vaccination is followed some weeks later by one or more "booster" vaccinations, the net effect of which is the production of vigorous cellular and humoral immune response.

The method of immunizing a mammal against lungworm disease involves administering to the mammal an effective amount of the foregoing immunogen. Administration may involve any procedure well-known in the art. Any immunization route which may be contemplated or shown to produce an appropriate immune response can be employed, in accordance with the present invention, although subcutaneous administration is preferred. Suitable administration forms include parenteral, intracutaneous or intramuscular injections or preparations suitable for oral, nasal or rectal administration.

The instant invention also relates to antibodies and antisera to natural DV 18, DV 18 fragments, recombinant DV 18, or DV 18 variants. Such antibodies and antisera are raised using standard vaccination regimes in appropriate hosts. The host is vaccinated with at least one antigen or vaccine of the present invention, with or without an adjuvant, to generate an immune response. The immune response may be monitored, for example, by measurement of the levels of antibodies produced, using standard ELISA methods.

In a preferred embodiment, production of polyclonal antisera is carried out using cattle as host. The host is bled on a regular basis and the antibody fraction purified from the blood by standard means, e.g., by protein A or protein G chromatography. In an alternative embodiment, the host is a mouse, and monoclonal antibody-producing hybridomas are prepared by standard means. See CURRENT PROTOCOLS IN IMMUNOLOGY, Coligan et al., Eds. John Wiley, New York, 1991) ch. 2.5. Monoclonal antibodies are then prepared from the hybridoma cells by standard means.

The invention also relates to a diagnostic kit which contains the above-described protein from D. viviparus and preferably at least one of the antibodies as described above in suitable containers.

Diagnostic kits for detection of *D. viviparus* infestation are prepared by providing at least one of the antibodies prepared above, together with a positive control standard of a known concentration of the antigen of the present invention. In one embodiment, the antigen positive control is the purified, naturally occurring DV18. The kit format conforms to a standard diagnostic format such as the ELISA format.

Table 1 is described as follows:

Table 1: Partial amino acid sequences of the isolated DV 18 protein from *Dictyocaulus viviparus*.

TPPAGVFYQGXSATPIA     (SEQ ID NO.: 1)

The amino acid adjacent to the N-terminus of SEQ ID NO. 1 is any one of the amino acids D, N, S, G or R.

LPIEYNE     (SEQ ID NO.: 3)

The amino acid adjacent to the N-terminus of SEQ ID NO.: 3 is any one of the amino acids N or S.

FRREWFQGDGWRRK     (SEQ ID NO.: 4)

The amino acid adjacent to the N-terminus of SEQ ID NO.: 4 is any one of the amino acids A or G. In addition, the 11th amino acid of SEQ ID NO.: 4(V) can also be methionine (M).

VFNAPYDDK     (SEQ ID NO.: 5)

The amino acid adjacent to the N-terminus of SEQ ID NO.: 5 is any one of the amino acids D or I.

XPPAGVFYQGWSATPIANGSLG     (SEQ ID NO.: 6)

The amino acid adjacent to the N-terminus of SEQ ID NO. 6 is any one of the amino acids D, S, G or A.

TYHIK     (SEQ ID NO.: 7)

The amino acid adjacent to the N-terminus of SEQ ID NO. 7 is any one of the amino acids D or H.

IINASGRRIGWAIK     (SEQ ID NO.: 8)

EXAMPLES

The invention will now be explained in more detail with the aid of the Figure and the Examples, without being restricted thereto.

Normal sera and infection sera from cattle which were infected with gastrointestinal nematodes such as Ostertagia ostertagi and Cooperia oncophora, and also the lungworm *Dictyocaulus viviparus*, were used for identifying protein DV 18.

Chromatographically separated protein fractions, which were obtained from homogenized, adult lungworms, were subjected to further fractionation by means of SDS polyacrylamide gel electrophoresis and immobilized on Immobilon P membranes (semidry blotting). The lungworm-specific protein DV 18 was subsequently detected with the specific infection sera and then purified further using an analytical gel filtration column. The purity of the protein fraction was checked in silver-stained SDS polyacrylamide gels (Phast gels). The protein concentration in electrophoretically pure DV 18 fractions was determined by means of a BCA protein assay, and the fractions were deep-frozen at −85° C. Helminth-naive cattle were in each case vaccinated with a defined quantity of purified DV 18. 1 week after the second vaccination, the cattle were challenged with *Dictyocaulus viviparus* L3 larvae. Unvaccinated animals served as control. 4 weeks after the challenge, the cattle were slaughtered, after which the number of adult worms in the lung was determined and the length of the male and female worms were measured. The reduction in the number of adult worms as compared with the unvaccinated control was defined as the measure of the immune protection. Purified DV 18 enables a dictyocaulosis to be detected in an ELISA up to 3 months after infection.

After evaluation of the parasitological parameters it was found that the worm burden in the vaccinated group was reduced by 80% and that adult worms were significantly smaller than in the control group (reduction 40%). Furthermore, the excretion of L1-larvae in the vaccinated group was significantly reduced.

The PCR conditions are determined in preliminary experiments using methods which are known to any skilled person.

Example 1
Preparation of infection sera

Six-month old Helminth-naive cattle were infected with differing doses of third-stage larvae of various nematode species (*Dictyocaulus viviparus, Ostertagia ostertagi* and *Cooperia oncophora*). In the Dictyocaulus group, the infection doses were 2500, 1250 and 500 larvae/calf; 3 animals were used per dose. For the Ostertagia group, infection doses of 70 000, 30 000 and 15 000 larvae/calf were chosen. In addition to a non-infected group (=negative control), a mixed group was also included in which each calf was infected with 2 500 Dictyocaulus larvae, 10 000 Ostertagia larvae and 10 000 Cooperia larvae. Serum samples, which were stored at −25° C. in aliquoted form, were obtained from each calf on days DO (=day of infection), D +21, D +40, D +56, D +70, D +84, D +98 and D +112. The sera were used for identifying the Dictyocaulus antigen DV 18 in electrophoretically and chromatographically separated protein fractions and also for assessing specificity.

Example 2
Isolation of adult lungworms

Six-month old, helminth-naive cattle were in each case infected orally with 5000 third-stage *Dictyocaulus viviparus* larvae; on the next day, the animals were given the same infection dose. 28 days after infection, the cattle were slaughtered and, following dissection, adult worms were collected from the lungs. The worms were subsequently washed 3×with phosphate-buffered sodium chloride solution, weighed and stored at −85° C. until work-up.

Example 3
Extraction of DV 18 from adult lungworms 9.5 g of frozen worm mass were ground in a mortar under liquid $N_2$ and then homogenized with 19 ml of 0.025 M tris-HCl solution, pH 7.4, +2 mM Pefabloc® using an Ultraturrax. In order to remove coarse tissue constituents, the homogenate was centrifuged at 3010 g and 4° C. for 15 min and the pellet was discarded. The supernatant was centrifuged at 39 800 g and 4° C. for 20 min and the supernatant which resulted from this centrifugation was centrifuged once again at the same g number for 10 min. After filtration (pore size 1.2 µm), the clear supernatant was deep-frozen at −25° C. in 4 ml aliquots.

Example 4
Preparative gel filtration

The 4ml aliquots mentioned in Example 3 were individually fractionated in a Pharmacia FPLC System using a preparative gel filtration column (column type: XK 26/100; separation medium: Sephacry® HR 200, column volume:

480 ml). 0.1 M Tris-HCl solution, pH 7.4, was used as the mobile phase. The fractions having the retention volumes 286–306 ml were collected and concentrated using ultrafiltration modules (Centriprep® 10 from Amicon). Protein DV 18 was detected using an amplified Western Blot.

Example 5
Western Blot analysis

The concentrated Sephacryl HR 200 fraction was mixed with reducing SDS buffer in a ratio of 1:2; of this, 40 µl were loaded into each sample well on an SDS Excel gel (from Pharmacia). The electrophoresis was carried out under standardized running conditions (600V, 50 mA, 30 W, running time: 90 min) in a Multiphor II chamber (from Pharmacia). The electrophoretically fractionated proteins were transferred by means of semidry blotting (Tovey ER, Baldo BA. Electrophoresis. 8, 1987, 384–387) onto Immobilon P membranes (transfer conditions: 45 min, constant current strength 0.8 mA/cm$^2$) and, after a 24-hour blocking phase using 3% bovine serum albumin in Tris-buffered sodium chloride solution (TBS), incubated for 1 hour with a Dictyocaulus-specific immune serum (obtained on D +40, see Example 1) diluted 1:20. Normal bovine serum (1:20 dilution) was used as the negative control. After having been washed 3 times with TBS+0.05% Tween 20, the blot membrane was incubated for 1 hour with a biotin-labeled goat anti-cattle IgG(H+L) antibody (1:500; from Pierce). After having been washed 3 times (TBS+0.05% Tween 20), the membrane was incubated for 1 hour with the enzyme conjugate biotin-streptavidin-alkaline phosphatase (1:2500; from Pierce). Substrate development was carried out using the Biorad substrate kit.

Example 6
Analytical gel filtration

Figure 1:
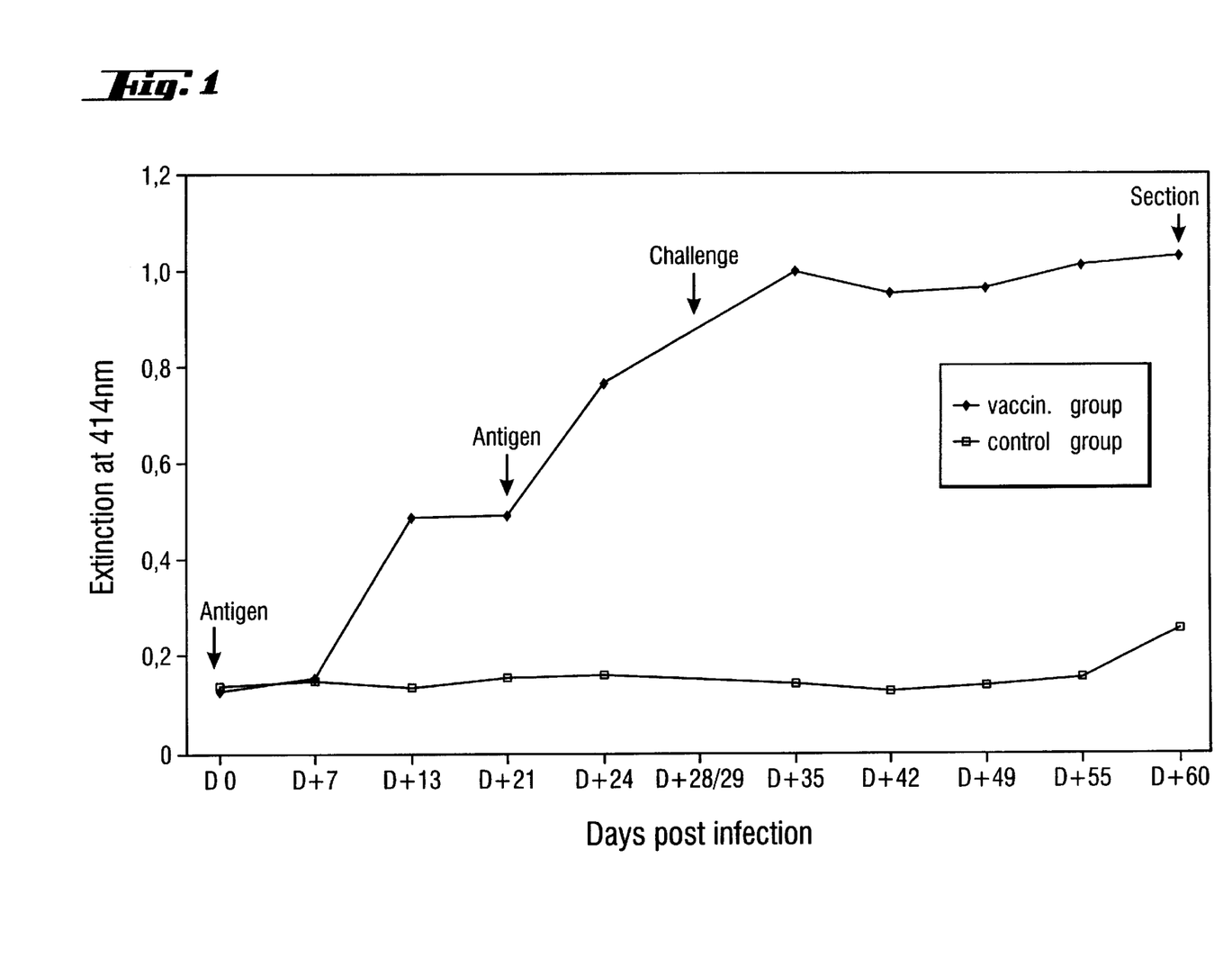
FIG. 1 is a representation of detection of protective, dictyocaulus-specific antibody titers with and without previous vaccination with antigen DV 18. Y-axis: wavelength.
Figure 2:
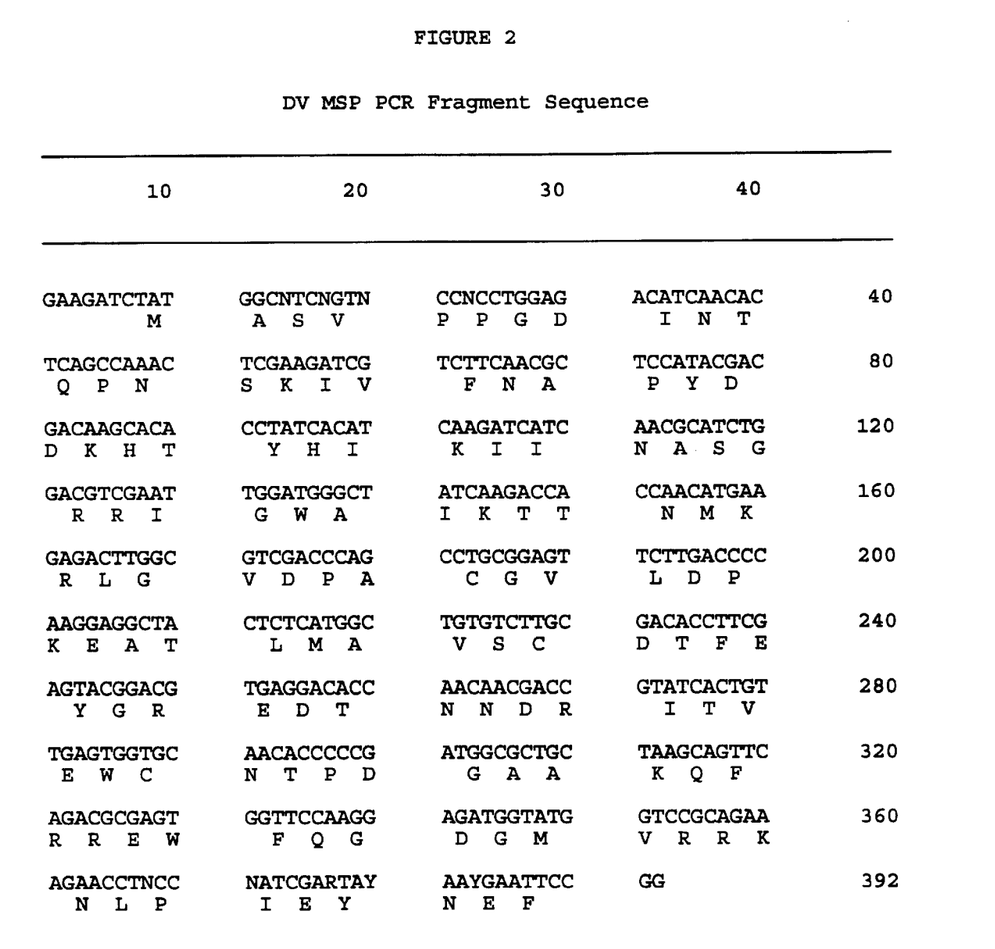
FIG. 2 represents cDNA and amino acid sequences corresponding to the DV 18 gene and protein (SEQ ID NOS: 13 and 14).

Following the immunological detection of DV 18, the protein was subjected to further purification in an FPLC system. A Superose 12 HR 10/30 column from Pharmacia was used for this purpose; PBS was used as the mobile solvent. 300 µl of the fraction which was concentrated in Example 4 were loaded on the column for each run; the flow rate was 0.3 ml/min. A retention volume of 13.5 ml was measured for DV 18.

Example 7

Purity demonstration and molecular weight determination

The FPLC fraction having a retention volume of 13.5 ml was analyzed in the Phast system under standardized conditions using an SDS polyacrylamide gel (8–25% Phast SDS gel) (from Pharmacia). The "Silver Stain SDS-PAGE Standards, low range" Biorad kit was used as molecular weight marker. After the electrophoresis, DV 18 was visualized by means of silver staining (Silverstain Kit, from Pharmacia). The molecular weight determination was carried out with a video densitometer (Molecular analyst, from Biorad) using a "Profile analyst II" evaluation program. DV 18 was calculated to have a molecular weight of 17 500±1 500 daltons.

Example 8

Determination of the isoelectric point

DV 18 which was isolated as described in Example 6 was diluted with ultrahigh-purity water and loaded onto previously prepared focusing gels (pH 3–10 IEF Phast gels, from Pharmacia). The focusing in the Phast system was effected under standardized conditions. Marker proteins having defined isoelectric points ("Biorad pI Kit", pH 3.5–9.3; from Pharmacia) were included for determining the isoelectric point of DV 18. An isoelectric point of 5.5±0.3[ was found.

Example 9

Detection of glycosylation

The specific binding of lectins of known carbohydrate specificity was exploited for the purpose of identifying N-glycan chains or O-glycosidically bonded carbohydrate structures. The digoxigenin glycan differentiation kit from Boehringer Mannheim was used for the analysis. DV 18 which was immobilized on a blot membrane (Immobilon P® membrane) and characteristic glycoproteins were visualized by means of reversible protein staining (Ponceau S staining), marked with a pencil and then decolorized once again. Following incubation with digoxigenin-labeled lectins, carbohydrate structures were detected using an alkaline phosphatase-labeled anti-digoxigenin antibody. DV 18 did not react with specific lectins and is evidently not glycosylated.

Example 10

Amino acid sequence analysis

DV 18 (35 μg) which was isolated as described in Example 6 was sequenced according to standard procedures. The following amino acid partial sequences were identified:

TPPAGVFYQGXSATPIA (SEQ ID NO.: 1)

The amino acid adjacent to the N-terminus of SEQ ID NO. 1 is any one of the amino acids D, N, S, G or R.

XLGVDPASGVLDPKEATIMA (SEQ ID NO.: 2)

LPIEYNE (SEQ ID NO.: 3)

The amino acid adjacent to the N-terminus of SEQ ID NO.: 3 Is any one of the amino acids N or S.

FRREWFQGDGWRRK (SEQ ID NO.: 4)

The amino acid adjacent to the N-terminus of SEQ ID NO.: 4 is any one of the amino acids A or G. In addition, the 11th amino acid of SEQ ID NO.: 4(V) can also be methionine (M).

VFNAPYDDK (SEQ ID NO.: 5)

The amino acid adjacent to the N-terminus of SEQ ID NO.: 5 is any one of the amino acids D or I.

XPPAGVFYQGWSATPIANGSLG (SEQ ID NO.: 6)

The amino acid adjacent to the N-terminus of SEQ ID NO. 6 is any one of the amino acids D, S, G or A.

TYHIK (SEQ ID NO.: 7)

The amino acid adjacent to the N-terminus SEQ ID NO. 7 is any one of the amino acids D or H.

IINASGRRIGWAIK (SEQ ID NO.: 8)

Example 11

Demonstration that DV 18 has a protective effect

Four-month old, helminth-naive bull calves (indoor-reared, coproscopic detection negative) were each vaccinated subcutaneously with 35 μg of purified native DV 18. Three weeks later, each animal was given a booster vaccination of 20 μg of antigen/calf. One week after the 2nd vaccination, each of the animals was challenged with 2×750 *Dictyocaulus viviparus* L3 larvae. Unvaccinated animals were used as control. 28 days after challenge, the animals were slaughtered and the number of adult worms in the lung was determined; at the same time, the lengths of intact male and female worms were measured. Beginning with the vaccination experiment, blood sampling and serum isolation took place weekly. The specific antibody titers were determined in an ELISA (see Example 12) (see FIG. 1). The number of adult worms was found to be reduced by 80% in the vaccinated group (n=6 animals). Morphologically, adult worms were significantly smaller as compared with the control group (40% reduction).

Example 12

ELISA for the serological detection of dictyocaulosis

ELISA plates ("Maxisorb®" from Nunc) were coated with a concentration of 5 µg of DV 18/ml of PBS; the reaction volume was 100 µl per well. After an incubation of 1 hour at 37° C., the plates were washed 3 times in an ELISAwasher® (from Biorad), with the wash volume being 200 µl per well. Ultrahigh-purity water+0.1% Tween 20 was used as the wash solution. Nonspecific binding sites were blocked by incubating the plates (at room temperature for 3 hours) with a proteolytic mixture of gelatin (from Boehringer Mannheim). The plates were incubated on a microtiter plate shaker at a shaking frequency of 300 rpm. After the plates had been washed 3 times, the wells were loaded with a 1:200 dilution of the serum samples; the sera were thawed immediately before use, mixed thoroughly and then diluted with sterile PBS. The serum samples were incubated at room temperature for 1 hour with shaking. After the plates had been washed 3 times, peroxidase-conjugated, polyclonal rabbit antibodies against bovine IgG (Fc fragment-specific; from Dianova) were used in a dilution of 1:10 000 for detecting Dictyocaulus-specific antibodies; the incubation lasted 30 min. The plates were subsequently washed 4 times and then incubated with substrate solution (composition: 5 ml of 10-fold concentrated ABTS buffer (from Boehringer Mannheim)+45 ml of ultrahigh-purity water+1 ABTS tablet). Substrate development took place at room temperature and was monitored every 10 min at 414 nm in an ELISA Reader. Dictyocaulus-specific antibodies were detectable in the ELISA 28 days after a lungworm infection at the earliest and were still detectable with confidence at 3 months after the infection. Cross reactions with gastrointestinal nematodes such as *Ostertagia ostertagi* and *Cooperia oncophora* were not observed.

The embodiments set forth above are to illustrate the invention and are not intended to limit the methods and products of the present invention. Additional embodiments and advantages within the scope of the claimed invention will be apparent to one of ordinary skill in the art.

German priority application 19601754.8 filed on Jan. 19, 1996, including the specification, drawings, claims and abstract, is hereby incorporated by reference.

What is claimed is:

1. An isolated protein of *Dictyocaulus viviparus*, which has an apparent molecular weight of between 16,000 and 19,000 by SDS polyacrylamide gel electrophoresis, and comprises the amino acid sequence of SEQ ID NO: 3, or a fragment of said protein which contains SEQ ID NO: 3 and which will specifically bind to antibodies raised against the protein.

2. The protein of claim 1, which has the amino acid sequence of SEQ ID NO: 14.

3. The protein of claim 1, which is non-glycosylated.

4. An immunoassay for detecting a *Dictyocaulus viviparus* specific antibody in a sample comprising contacting said sample with the protein or fragment thereof of claim 1, and detecting the binding of said antibody to said protein or fragment.

5. The immunoassay of claim 4, wherein said sample is bovine serum.

6. An immunogenic composition comprising the protein or fragment thereof according to claim 1, together with a pharmaceutically acceptable carrier.

7. The immunogenic composition of claim 6, further comprising an adjuvant.

8. A method for immunizing a mammal against dictyocaulosisa, comprising administering to said mammal an amount of the protein or fragment thereof according to claim 1, said amount being sufficient to elicit an immune response in said host against dictyocaulosisa.

9. The method of claim 8, wherein said mammal is bovine.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 17 amino acids
        (B) TYPE: amino acid
        (C) STRANDEDNESS: single
        (D) TOPOLOGY: linear     (xi) SEQUENCE DESCRIPTION: SEQ ID NO:1:

Thr Pro Pro Ala Gly Val Phe Tyr Gln Gly Xaa Ser Ala Thr Pro Ile
1            5                  10                 15

Ala (2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear     (xi) SEQUENCE DESCRIPTION: SEQ ID NO:2:

Xaa Leu Gly Val Asp Pro Ala Ser Gly Val Leu Asp Pro Lys Glu Ala
1            5                  10                 15

Thr Leu Met Ala
            20

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:3:

Leu Pro Ile Glu Tyr Asn Glu
1               5

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:4:

Phe Arg Arg Glu Trp Phe Gln Gly Asp Gly Trp Arg Arg Lys
1               5                  10

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:5:

Val Phe Asn Ala Pro Tyr Asp Asp Lys
1               5

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:6:

Xaa Pro Pro Ala Gly Val Phe Tyr Gln Gly Trp Ser Ala Thr Pro Ile
1               5                  10                  15

Ala Asn Gly Ser Leu Gly
            20

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:7:

Thr Tyr His Ile Lys
1               5

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:8:

Ile Ile Asn Ala Ser Gly Arg Arg Ile Gly Trp Ala Ile Lys
1               5                  10

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (xi) SEQUENCE DESCRIPTION: SEQ ID NO:9:

```
GAAGATCTRT NGTCTTYAAY GCNCC                                               25
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION: SEQ ID NO:10:

```
CCGGAATTCR TCNCCCTGGA ACCAYTC                                             27
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION: SEQ ID NO:11:

```
CCGGAATTCR TTRTAYTCGA TNGGYAA                                             27
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION: SEQ ID NO:12:

```
CCGGAATTCR TTRTAYTCGA TNGGNAA                                             27
```

(2) INFORMATION FOR SEQ ID NO:13:

(i) SEQUENCE CHARACTERISTICS:
        (A) LENGTH: 392 base pairs
        (B) TYPE: nucleic acid
        (C) STRANDEDNESS: single
        (D) TOPOLOGY: linear     (ix) FEATURE:
        (A) NAME/KEY: CDS
        (B) LOCATION: 9..389

(xi) SEQUENCE DESCRIPTION: SEQ ID NO:13:

```
GAAGATCT ATG GCN TCN GTN CCN CCT GGA GAC ATC AAC ACT CAG CCA AAC          50
         Met Ala Ser Val Pro Pro Gly Asp Ile Asn Thr Gln Pro Asn
          1               5                  10

TCG AAG ATC GTC TTC AAC GCT CCA TAC GAC GAC AAG CAC ACC TAT CAC           98
Ser Lys Ile Val Phe Asn Ala Pro Tyr Asp Asp Lys His Thr Tyr His
 15                  20                  25                  30

ATC AAG ATC ATC AAC GCA TCT GGA CGT CGA ATT GGA TGG GCT ATC AAG          146
Ile Lys Ile Ile Asn Ala Ser Gly Arg Arg Ile Gly Trp Ala Ile Lys
              35                  40                  45
```

```
ACC ACC AAC ATG AAG AGA CTT GGC GTC GAC CCA GCC TGC GGA GTT CTT        194
Thr Thr Asn Met Lys Arg Leu Gly Val Asp Pro Ala Cys Gly Val Leu
            50                      55                  60

GAC CCC AAG GAG GCT ACT CTC ATG GCT GTG TCT TGC GAC ACC TTC GAG        242
Asp Pro Lys Glu Ala Thr Leu Met Ala Val Ser Cys Asp Thr Phe Glu
        65                      70                  75

TAC GGA CGT GAG GAC ACC AAC AAC GAC CGT ATC ACT GTT GAG TGG TGC        290
Tyr Gly Arg Glu Asp Thr Asn Asn Asp Arg Ile Thr Val Glu Trp Cys
    80                      85                  90

AAC ACC CCC GAT GGC GCT GCT AAG CAG TTC AGA CGC GAG TGG TTC CAA        338
Asn Thr Pro Asp Gly Ala Ala Lys Gln Phe Arg Arg Glu Trp Phe Gln
 95                 100                 105                 110

GGA GAT GGT ATG GTC CGC AGA AAG AAC CTN CCN ATC GAR TAY AAY GAA        386
Gly Asp Gly Met Val Arg Arg Lys Asn Leu Pro Ile Glu Tyr Asn Glu
                115                 120                 125

TTC CGG                                                                392
Phe (2) INFORMATION FOR SEQ ID NO:14:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:14:

Met Ala Ser Val Pro Pro Gly Asp Ile Asn Thr Gln Pro Asn Ser Lys
 1               5                  10                  15

Ile Val Phe Asn Ala Pro Tyr Asp Asp Lys His Thr Tyr His Ile Lys
                20                  25                  30

Ile Ile Asn Ala Ser Gly Arg Arg Ile Gly Trp Ala Ile Lys Thr Thr
            35                  40                  45

Asn Met Lys Arg Leu Gly Val Asp Pro Ala Cys Gly Val Leu Asp Pro
        50                  55                  60

Lys Glu Ala Thr Leu Met Ala Val Ser Cys Asp Thr Phe Glu Tyr Gly
 65                 70                  75                  80

Arg Glu Asp Thr Asn Asn Asp Arg Ile Thr Val Glu Trp Cys Asn Thr
                85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Glu Phe
        115                 120                 125
```